United States Patent [19]

Mimura et al.

[11] Patent Number: 5,360,411
[45] Date of Patent: Nov. 1, 1994

[54] LIQUID MEDICINE INJECTING DEVICE

[75] Inventors: Jinko Mimura, Niiza; Hideya Sato, Tokyo, both of Japan

[73] Assignees: Opto Tech Co., Ltd.; Aubex Corporation, both of Tokyo, Japan

[21] Appl. No.: 134,433

[22] Filed: Oct. 12, 1993

[30] Foreign Application Priority Data

Oct. 12, 1992 [JP] Japan ................... 4-272815

[51] Int. Cl.⁵ ............................ A61M 5/152
[52] U.S. Cl. ................... 604/246; 604/153; 604/280
[58] Field of Search ............ 604/153, 236, 237, 246, 604/31, 247, 280

[56] References Cited

U.S. PATENT DOCUMENTS

| | | | |
|---|---|---|---|
| 4,795,439 | 1/1989 | Guest | 604/280 |
| 4,834,705 | 5/1989 | Vaillancourt | 604/236 |
| 4,919,167 | 4/1990 | Manska | 604/247 |
| 4,997,420 | 3/1991 | LeFeure | 604/246 |
| 5,014,750 | 5/1991 | Winchell et al. | 604/246 |
| 5,061,243 | 10/1991 | Winchell et al. | 604/246 |
| 5,061,253 | 10/1991 | Yoshida | 604/236 |
| 5,176,360 | 1/1993 | Winchell et al. | 604/246 |
| 5,224,938 | 7/1993 | Fenton, Jr. | 604/247 |

*Primary Examiner*—Paul J. Hirsch
*Attorney, Agent, or Firm*—Lowe, Price, LeBlanc & Becker

[57] ABSTRACT

A liquid medicine injecting device for constantly feeding a liquid medicine into a human body at a certain degree. The liquid medicine stored in a liquid medicine receiving portion is fed out therefrom by a pressure means to be supplied into the human body through a flow amount control means and a human body fitting tool such as a needle. Even if there are contaminant and the like in the liquid medicine or if the flow amount control means is folded, twisted, or pressured, the tube is not blocked up to thereby function as a capillary tube and a member for controlling flow amount with a simple structure so that a high productivity and a easy handling can be obtained.

17 Claims, 6 Drawing Sheets

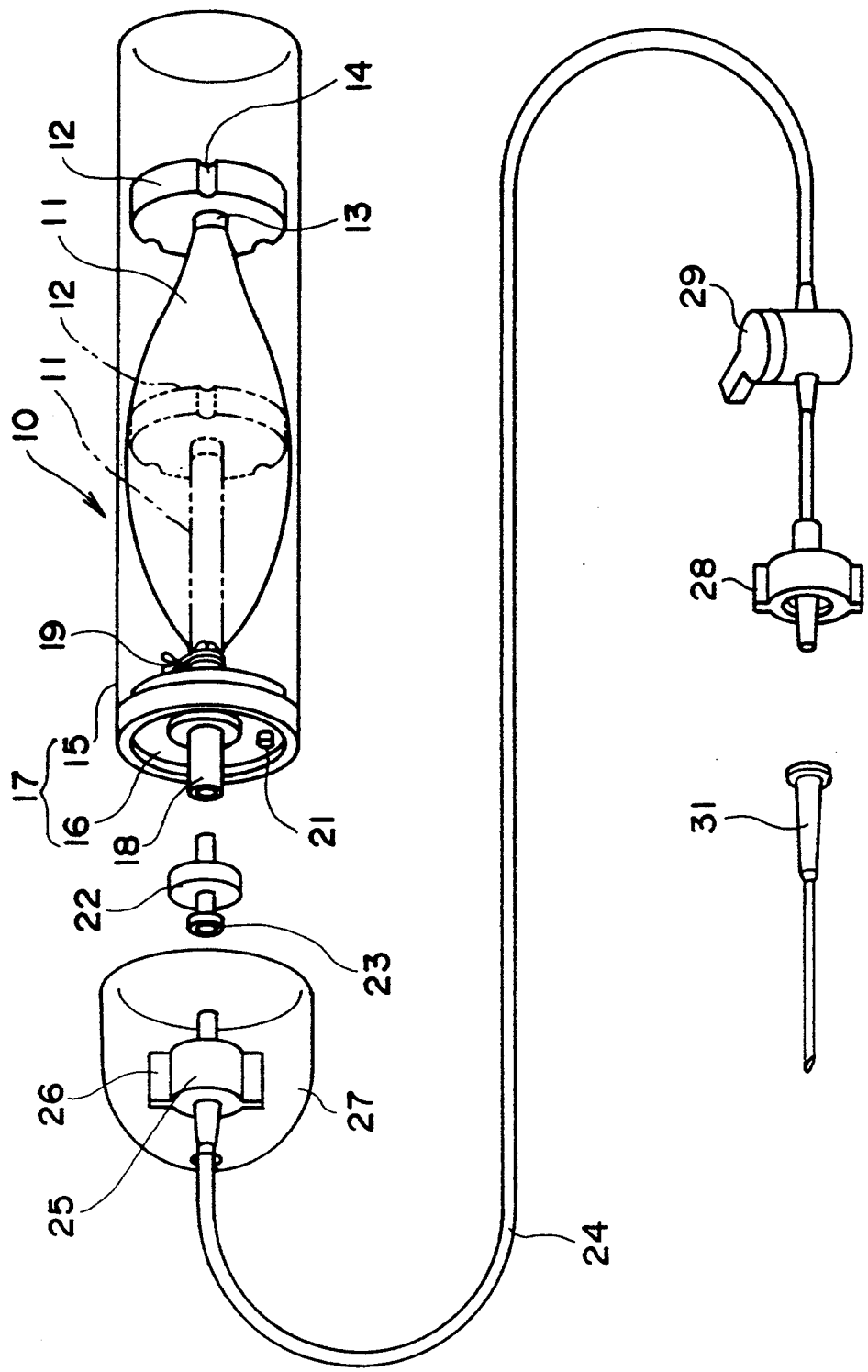

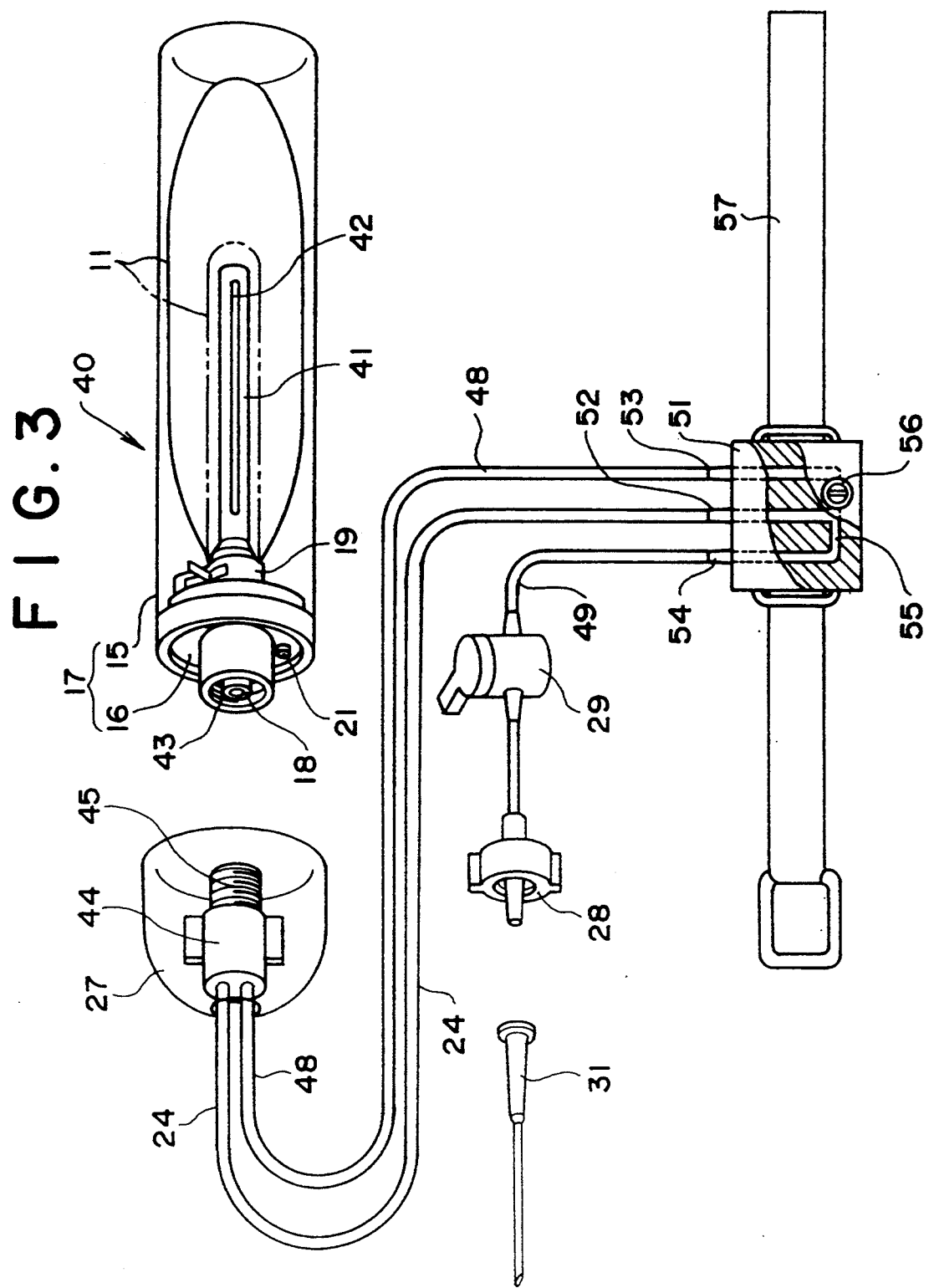

LIQUID MEDICINE INJECTING DEVICE

BACKGROUND OF THE INVENTION

1. Field of the Invention

This invention relates to a liquid medicine injecting device for feeding a liquid medicine stored in a liquid medicine receiving portion and, more particularly, to a modification of a known device for controlling flow amount of the liquid medicine when feeding the liquid medicine into human body.

2. Description of the Related Art

The liquid medicine injection into the human body has previously been conducted manually or automatically by a syringe storing therein the liquid medicine through a needle or catheter or by a drip-feed solution instillator.

The use of such a conventional device needed several minutes or hours for both a patient and a doctor or nurse the condition of which causes the patient to feel pain because of long injection period of time or to remain still and the doctor or nurse to hold the syringe long time or to check drip-feed amount.

There were some prior arts regarding to liquid medicine injectors which do not require the patient and the doctor or the nurse to remain still and provide a preferable handling because of small in size (cf. Japanese Patent Laid-open No. Sho56-102252, Japanese Patent Publication NO. Hei61-51901, Japanese Patent Laid-open No. Sho62-11465, and Japanese Patent Laid-open No. Hei2-307477).

Most of these conventional liquid medicine injectors included an elastic balloon to store therein the liquid medicine one end of which is used as an inlet to allow the liquid medicine flow into the balloon and the other of which is used as an outlet. The inlet of the balloon is provided with a leakage preventing system defined by a check-valve regulating the flow of the liquid medicine in one-way and a partition made from a soft rubber.

The balloon is intended to flow out the liquid medicine stored therein from the outlet when it deflates to supply the liquid medicine into the human body through a needle as a human body fitting tool.

However, it has been understood that the outlet of the conventional liquid medicine injector did not work well as a member for controlling flow amount in practical use.

Taking for an instance, the flow amount control system for liquid medicines in Japanese Patent Laid-open No. Sho56-102252 employs a short length pipe the inner diameter of which is changeable. But, such a short pipe was not preferable for precise flow control.

The flow amount control system for liquid medicines in Japanese Patent Publication No. Sho61-51901 employs a diaphragm which can change a diameter of inlet hole provided in a pipe wall of a cylindrical body where a balloon is attached and further can change an area of outlet inner diameter of the cylindrical body in response to the inner pressure of the balloon.

However, it was known that the inlet hole provided in the pipe wall was not thick to control flow amount and the diaphragm was not produced easily in practical use.

The flow amount control system for liquid medicines in Japanese Patent Laid-open No. Sho62-11465 employs a flow amount control wringable valve at the outlet. But, this is still impossible to precisely control flow amount.

The flow amount control system for liquid medicines in Japanese Patent Laid-open No. Hei2-307477 employs a thin tube inserted in a liquid medicine receiving portion to control flow amount. The thin tube was generally made of a stainless or glass tube having the diameter of 0.05 mm, but involved the following problems.

When one considers to control flow amount by utilizing a thin tube, the tube should have the inner diameter of 0.05 mm, the outer diameter of 0.020 mm and the length of 1000 mm under a 1400 mm water column to obtain the constant flow of 0.5 ml/hr. But, such a tube can not be obtained easily and is not metired in handling.

These stainless thin tube can be made of a drawn tube, but the drawn tube generally involves burr on the inner wall surface thereof which is not preferable for obtaining precise flow control.

When the hole diameter of the stainless steal thin tube will become lower than 0.05 mm, the outer diameter thereof may become 0.1–0.15 mm which is too thin to connect other members such as a liquid medicine tube, a filter and a main body. If desired to use the thin stainless steal tube, it will be available to be used after increasing the diameter but it requires to coat the tube.

When using a glass tube, it is too hard to be curved as the stainless steal thin tube so that the preferable length of the glass tube should be until 100 mm. It is therefore necessary to make the area small in size but which may cause difficulties in manufacturing.

Further, the material is tend to be broken easily in handling. The glass tube does not have an elastic property and is weak in shock so that the assembling thereof should be careful.

As has been described above, the glass and stainless thin tube can not be manufactured easily and does not have a large outer diameter to obtain 100 micrometer inner diameter.

The purpose of the present invention is to provide a liquid medicine injecting device capable of controlling flow amount precisely with a simple structure as described below.

SUMMARY OF THE INVENTION

Accordingly, a liquid medicine injecting device according to the present invention is characterized to have: a liquid medicine receiving portion to store therein a liquid medicine; a pressure means for pressurizing the liquid medicine; flow amount control means applied to be connected to the liquid medicine receiving portion at one end thereof and made from a thermoplastic resin having a different sectional configuration and a predetermined length for conducting two functions as a capillary tube and a member for controlling flow amount all together; and a human body fitting tool connecting to the other end of the flow amount control means so that the liquid medicine stored in the liquid medicine receiving portion is fed into a human body through the flow amount control means and the human body fitting tool.

Incidentally, a sectional configuration of the tube defining the flow amount control means is arranged by three sets of two different arborescent raised portions each of which is extending from an inner wall surrounding a base round hole.

A sectional configuration of the tube defining the flow amount control means is formed into a Y-shape, each stem of the Y being angularly intersecting each other at a same angle of 120 degrees. The Y-shaped opening may be formed by uneven surface. Incidentally, a short side of the each stem shape of the opening is kept within 0.01–0.1 mm and a ratio of (total Long side)/(Short side) becomes more than 3.

A sectional configuration of the tube defining the flow amount control means may be arranged by three tapered triangles with one roundly recessed portion at the base each of which extends from an inner wall surrounding a base round hole.

A sectional configuration of the tube defining the flow amount control means could be arranged by three sets of two different arborescent raised portions each of which is extending from an inner wall with uneven surface surrounding a base round hole.

The differentia degree of the tube is given by an expression of $\sqrt{(A/B)}$ on or more than 7, the "A" being an inside measurements of the opening and the "B" being an area of the opening.

The tube could be a single layered tube made from a thermoplastic resin tube selected one from polyethylene (PE), polypropylene (PP), polyacetal (POM), polycarbonate (PC), ABS, polyamide resin or polystyrene (PS) or a coated single layered tube with a thermoplastic polyurethane elastomer.

There may be provided a supplemental flow control means defined by a thermoplastic resin tube in a parallel state to the flow amount control means between the liquid medicine receiving portion and the human body fitting tool, the supplemental flow control means being provided with a flow on-off means for being manually opened and closed. Incidentally, the supplemental flow control means is made of a thick tube with a little pressure loss.

The liquid medicine receiving portion can be defined by a tubular rubber tunica elastica, and the pressure means is made by a contractile force of the tubular rubber tunica elastica one end of which directly or indirectly connects to the tube of the flow amount control means.

The liquid medicine receiving portion is received and closed up in a protective cover having a water repellent breathing filter. Incidentally, the protective cover is constructed by a cylinder and an associated cap, the liquid medicine receiving portion is a rubber tunica elastica both end of which are opened, and the pressure means is made by a contractile force of the tubular rubber tunica elastica one end of which directly or indirectly connects to the tube of the flow amount control means and the other end of which securely connects to a sliding element reciprocally moving in the protective cover. The rubber tunica elastica has a contractile force of from 1000 to 700 mm water column.

The liquid medicine receiving portion can be made by a rubber tunica elastica one end of which is opened and the other is closed, and the pressure means is made by a contractile force of the tubular rubber tunica elastica, and the device further has a liquid medicine feed pipe in the rubber tunica elastica which is adapted to fit the deflated rubber tunica elastica and connect to the tube of the flow amount control means.

BRIEF DESCRIPTION OF THE DRAWINGS

FIG. 1 is a perspective view depicting the liquid medicine injecting device according to the first embodiment of the present invention;

FIG. 3 is a perspective view depicting the second embodiment according to the present invention;

Figure 2A:
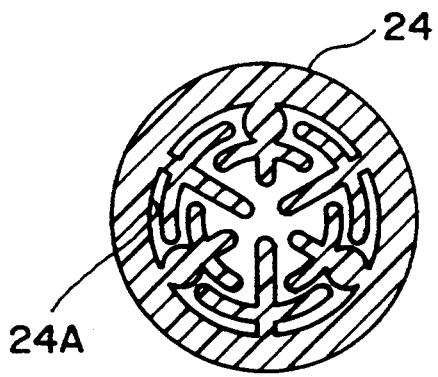
FIGS. 2(A)–2(E) are sectional views depicting sectional configurations of tubes applicable to the present invention.

Certain terminology will be used in the following description for convenience in reference only and will not be limiting. The words "up", "down", "right" and "left" will designate directions in the drawings to which reference is made. The words "in" and "out" will refer to directions toward and away from, respectively, the geometric center of the device and designated parts thereof. Such terminology will include derivatives and words of similar import.

DETAILED DESCRIPTION OF THE PREFERRED EMBODIMENT(S)

The preferred embodiments of the present invention will now be described with reference to the drawings. Incidentally, in the description of the following embodiments, the same reference numerals will be used to designate the same or similar components as those in the following first embodiment, so that the description will be omitted or simplified.

In FIG. 1 is described the first embodiment of a liquid medicine injecting device 10 according to the present invention. The liquid medicine injecting device 10 has a rubber tunica elastica 11, both longitudinal distal ends of which are terminated like a tube as a liquid medicine receiving portion and a pressure means. The rubber tunica elastica 1 is made from a material having enough stretch properties, wear-resistant properties and elevated toughness not to burst due to an external action and also being transparent or translucent. As known materials for the rubber tunica elastica 11, silicon rubber, lattices rubber or the like which can be obtained easily may be available.

As an average human vein is about a column of 600 mm, the rubber tunica elastica 11 is expected to have a pressure power from its shrinkage more that this column and preferably by a column of from 1000–7000 mm so as to a liquid medicine is fed into the human body. This is because that the column of less than 1000 mm does not provide a preferable injection control of a liquid medicine and the column of more than 7000 mm may be difficult to be given with all human strength, but naturally if such a high pressure will be available by any means, it will be no problem to apply thereto to apply the column of more than 7000 mm.

It can be seen that the rubber tunica elastica 11 is adhered, at the right distal opening thereof, to a tab exposed at the center on a surface of a sliding element 12. The sliding element 12 has a plural or three notches 14 on the peripheral surface to slidingly move on an inner surface of the cylinder 15 which has a bottom on one distal end thereof. The cylinder 15 is made from plastic, glass or so to safely cover the appearances of the rubber tunica elastica 11 and firmly has a cap 16 on the other distal end by a bonding agent, a seal by heat or an ultrasonic waves, or in a threadedly secured state thereon. The cylinder 15 and the associated cap 16 provide a protective cover 17 for the rubber tunica elastica 11.

There is provided through the central portion of the cap 16 a check-valve 18 on the markets. The check-valve 18 is provided as an inlet and outlet portion for a liquid medicine stored in the rubber tunica elastica 11. The valve 18 is adapted to connect to and be tightly engaged by a pinch 19 with the other opening of the rubber tunica elastica 11 through a portion of the check-valve 18 projecting from the cap 16 and disposing into the cylinder 15.

Accordingly, since the rubber tunica elastica 11 is closed up tightly in the protective cover 17 defined by the cylinder 15 and the cap 16, even if the rubber tunica elastica 11 will be unexpectedly busted, the liquid medicine maintained in the protective cover 17 will never flow out of the cover 17.

The cap 16 is further provided with a water repellent breathing filter 21 which does not pass any liquid therethrough but to do a gas or an air effectively. It is therefore that the stored liquid medicine in the protective cover 17 does not flow out through the filter 21. Incidentally, the water repellent breathing filter 21 could be made of a synthetic fiber fabric which is water-repellent finished and has a enough resistance to acids.

It will be further noted that the left opening of the check-valve 18 receives therein a liquid medicine filter element 22 to open the check-valve 18 to pass through the liquid medicine. The filter element 22 has therein a known filter (not-shown) to remove dust contained in the liquid medicine and is provided with a joint 23 at the left opening as shown in FIG. 1.

The joint 23 formed on the filter element 22 is provided to receive therein and release therefrom a connector 25 which is secured to an end of a thermoplastic resin tube 24 as a flow amount control means characterized in the present invention.

The strong enough interconnection between the connector 25 and the joint 23 of the filter element 22 is carried out by utilizing a wing portion 26. It will be noted from FIG. 1 that the connector 25 is covered by and kept in a round-shaped transparent cap 27 which can be detachably mounted on the cap 16 attached to the cylinder 15.

The tube 24 is also connected to another connector 28 same as the connector 25 and, if necessary, it is further provided with a cock 29 as a flow on-off means on its half way to open and shut the flow way in the tube 24. The flow on-off means can be replaced with another means such as a change-over valve, a clothespins or so which can allow or stop a flow of the liquid medicine in the tube 24.

At the forward end of the connector 28 is detachably provided a needle 31 as a human body fitting tool. In this state, the rubber tunica elastica 11 as the liquid medicine receiving portion relates to the needle 31 as the human body fitting tool via the thermoplastic resin tube 24 as the flowing amount control means.

The thermoplastic resin tube 24 could be a single layer tube or a coated tube considering reinforcement and handling. The tube 24 may be made from polyethylene (PE), polypropylene (PP), polyacetal (POM), polycarbonate (PC), ABS, polyamide resin, polystyrene (PS) or so. The preferable coating material should show a enough flexibility as a thermoplastic resin elastomer like a polyolefine (LDPE, LLDPE) elastomer, a thermoplastic polyurethane elastomer, a soft vinyl chloride resin, or a EVA.

The sectional view of the tube 24 does not show a circular configuration as in the conventional flowing amount control means but a complicated configuration as depicted in FIGS. 2(A)-2(E).

It will be noted from FIG. 2(A) that an opening 24A of the tube 24 is arranged by three sets of two different arborescent raised portions each of which is extending from an inner wall surrounding a base round hole.

Figure 2B:
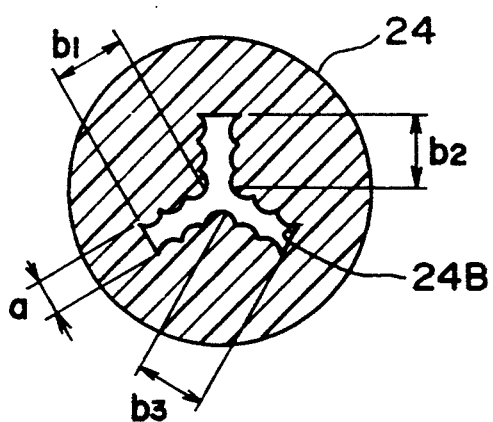

An opening 24B of the tube 24 depicted in FIG. 2(B) is generally formed into a Y-shape with uneven surface in its sectional view, each stem of the Y being angularly intersecting each other at a same angle of 120 degrees.

Figure 2C:
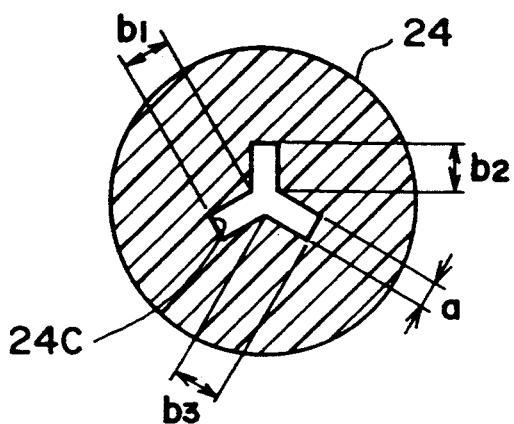

An opening 24C of the tube 24 depicted in FIG. 2(C) is similar to the opening 24B, but it does not have uneven surfaces and has shorter stems compared with the opening 24B.

When a short side of the each stem shape of the openings 24B and 24C describes with "a" and a long side of the same describes with "b1+b2+b3", the short side "a" may be kept within 0.01–0.1 mm and a ratio of Long side/Short side may be more than 3. When the ratio will be less than 3 preferable effects in flow amount control will not be obtained, when the short side will be less than 0.01 mm it will be resulted in an ineffective manufacturing, when the short side will be more than 0.1 mm a produced tube will have a small ratio of Long side/Short side, and if this ration will be intentionally increased, the flow amount will be increased over the expected value. Incidentally, it should be understood that there are other different opening configurations not being defined by the ration of Long side/Short side.

Figure 2D:
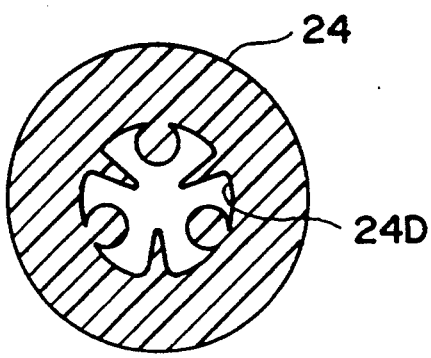

An opening 24D of the tube 24 depicted in FIG. 2(D) is arranged by three tapered triangles with one roundly recessed portion at the base, each of which extends from an inner wall surrounding a base round hole.

Figure 2E:
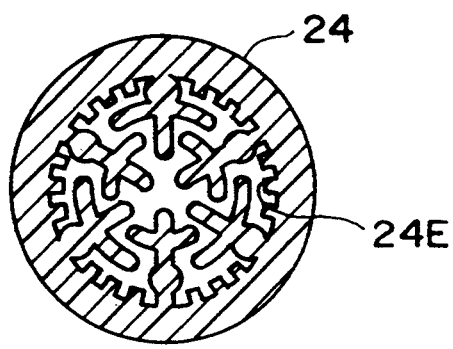

An opening 24E of the tube 24 depicted in FIG. 2(E) has a modified configuration from that of the opening 24(A) and also provided with a plural projections as an internal toothed gear on an inner wall surrounding a base round hole.

An efficiency by such different configuration can be produced more depending upon an increase of differentia degree given by an expression of $\sqrt{(A/B)}$, wherein the A means an inside measurements of the opening and wherein the B means an area of the opening. The above-described openings 24A–24E have the differentia degree on or more than 7, respectively.

The above-mentioned complicated configurations of the openings in the tube 24 can be manufactured by using a die taught in the Japanese Patent Application Laid-open No. Sho51-21927.

While the operation of the device will be obvious to those skilled in the art, a brief explanation of the operation will be given for convenience.

Before feeding the liquid medicine into the rubber tunica elastica 11 as a liquid medicine receiving portion, the round-shaped transparent cap 27 is taken off from the cover 17 and the filter element 22 is also removed from the check-valve 18. It will be noted from FIG. 1 that the rubber tunica elastica 11 deflates as described by the two-dashed line.

The intended liquid medicine originally stored in a syringe (not-shown) can be transferred into the inside of the inflatable rubber tunica elastica 11 by sticking a needle of the syringe into the check-valve 18 from the left side to open the check-valve 18. As the rubber tunica elastica 11 become inflated within the cylinder 15, the sliding element 12 moves longitudinally in the cylinder 15 smoothly because of plural notches 14 thereon preventing an air resistance applied to the sliding element 12. It is naturally understood that the air originally contained in the cylinder 15 is fed out through the water repellent breathing filter 21 upon the gradual inflation of the rubber tunica elastica 11.

When the feeding of the liquid medicine through the check-valve 18 by using the syringe is completed, the needle of the syringe is drawn out from the check-valve 18 but the liquid medicine fed and stored in the rubber tunica elastica 11 will not leak out from the check-valve 18.

Next, the right end portion of the filter element 22, preliminary secured to the connector 25 of the thermoplastic resin tube 24 is coupled into the check-valve 18 whereby the liquid medicine stored in the rubber tunica elastica 11 become fed out, but the liquid medicine will not be fed out actually due to the cock 29 in an off state.

As the another connector 28 of the tube 24 is connected to the needle 31 and which is stuck into the human body, the cock 29 is opened whereby the liquid medicine is gradually fed into the human body as expected though the tube 24.

The preferable flow amount as expected is approximately 0.05 ml/hr but the flow amount could be changed to comply with user's necessities by selecting one of different opening configurations as already explained above, by considering a length of the tube 24, and by using a different liquid medicine having a different coefficient of viscosity.

When all liquid medicine stored in the rubber tunica elastica 11 are transferred into the human body, the next liquid medicine can be fed into the rubber tunica elastica 11 as in the same way already explained above to repeat the above mentioned operation by the liquid medicine injecting device 10.

Incidentally, if releasing an air remaining in the rubber tunica elastica 11 before the needle 31 is stuck to the human body, the cylinder 15 stands up so that the cap 16 of the cover 17 faces upwardly and the cock 29 is opened until the liquid medicine will be spilled out from the needle 31 to thereby release the air.

The above-mentioned embodiment has effects as follows.

More specifically, as the generally long thermoplastic resin tube 24 having one of different openings 24A-24E is used in the present invention, precise flow amount control is facilitated, which has not been obtained by the conventional short tube having a single round opening.

When the conventional tube having a single round opening therein is used between the liquid medicine receiving portion and the human body fitting tool to feed the stored liquid medicine into the human body, there is a potential danger that if the liquid medicine includes contaminant or if it is apt to be solidified, the conventional tube may be clogged up therewith completely, while by the tube 24 according to the present invention, such potential danger will not take place since the tube 24 has the different opening 24A-24E wherein all of the long side will not be clogged up. The tube 24 is strong enough to prevent folding or clogged state thereof by a heavy patient who lies down, which could not be prevented by the conventional tube having the single round hole. In a field of medical care, the liquid medicine injecting device 10 should be supplied on the basis of safety-first.

It can be said that the tube 24, according to the above-mentioned embodiment has two functions as a capillary tube and a member for controlling flow amount all together in the device 10, so that the whole structure of the present invention is simplified compared with the instrument comprising the conventional capillary tube and flow amount control means.

It is possibly remained to utilize a stainless or glass tube for obtaining characteristics as the capillary tube and achieving the preferable flow amount control, but there will be caused some problem that is broken, folded or awkward, but in the tube 24 made from a thermoplastic resin according to the present invention, the above-mentioned specially different opening 24A-24E can be produced manufacturely and is controllable, and it further serves both as the small flow amount control function and the capillary tube function.

As the rubber tunica elastica 11 as the liquid medicine receiving portion and the thermoplastic resin tube 24 as the flow amount control means are divisionally provided as best depicted in the drawings, a wide flow amount control can be made by considering the preferable different opening pattern and length of the tube 24.

In the conventional liquid medicine injecting device, when the rubber tunica elastica will be busted, the stored liquid medicine therein may be leaked out so that if a strong acid liquid medicine showing pH 2 will be used the leakage thereof should damage human skin and clothes severely. On the contrary, in the present invention, the rubber tunica elastica 11 is entirely covered by the protective cover 17 and the cap 16 is provided with the water repellent breathing filter 21 as has been described above, it prevents the possibility of the leakage of the liquid medicine.

Figure 4:
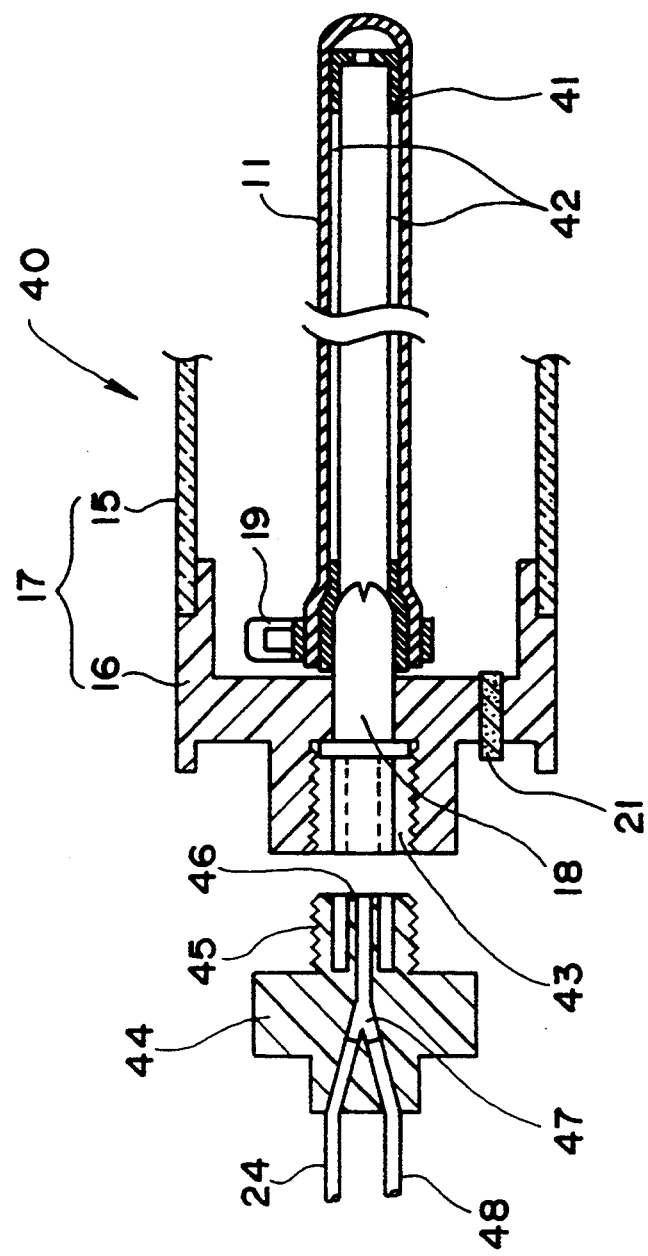
FIG. 4 is an enlarged sectional view showing a characteristic member shown in FIG. 3.

It is believed unnecessary to describe the structure in FIGS. 3–4 that is identical to the structure in FIGS. 1–2 because such is presented above. Turning now to the important differences that exist between the embodiment of FIGS. 3–4 and the embodiment of FIGS. 1–2, a liquid medicine injecting device 40 in the second preferable embodiment has modified portions in the rubber tunica elastica 11 and the feed amount control system.

It will be noted from FIGS. 3–4 that the protective cover 17 is defined by the cylinder 15 and the associated cap 16 including the check-valve 18 at its central portion which is provided with a liquid medicine feed pipe 41 extending into the inside of the cylinder 15. The feed pipe 41 includes plural slits 42 on its periphery to become utilized when the liquid medicine is fed from the check-valve 18 into the rubber tunica elastica 11.

The cap 16 has a female thread 43 to threadedly secure with a connector 44 which includes a corresponding male screw 45 and is adapted to connect with the thermoplastic resin tube 24 as the flow amount control means.

The connector 44 includes an applicator 46 in the male screw 45 to move into and open the check-valve 18. In FIG. 4, it will be noted that a flow path 47 branches off into two after the applicator 46 in the connector 44, one of which is connected with the tube 24 and the other of which is connected with a supplemental tube 48 to increase flow amount of the liquid medicine fed out from the rubber tunica elastica 11. The supplemental tube 48 is also made from the thermoplastic resin similarly to the tube 24 and has the same sectional pattern as made in the tube 24 or the conventional round opening. Further, the supplemental tube 48 can be replaced with a thick tube with low pressure loss, if desired.

Both tubes 24 and 48 are connected to a flow amount change device 51 by connection to connecting ports 52 and The flow amount change device 51 also includes a single outlet connecting port 54 to which an extended tube 49 is connected. The tube 49 has a cock 29 on its way and a connector 28 at the distal end thereof to which the needle 31 as a human body fitting tool is attached.

The respective ports 52-54 of the flow amount change device 51 are interconnected to each other through an inner path 55 which includes one cock 56 as the flow on-off means to optionally render the supplemental tube 48 to connect to the extended tube 49. Incidentally, the cock 56 is regularly in a closed state not to connect the supplemental tube 48 for the extended tube 49 but to connect the tube 24 for the tube 49.

Accordingly, when the cock 56 is kept in the closed state, the extended tube 49 become received a predetermined regulated flow amount of the liquid medicine limitedly from the tube 24 whereas, in the opened state, the supplemental flow of the liquid medicine from the tube 48 is added into the tube 49 if desired.

The flow amount change device 51, for example, is attached to the wrist by means of a wrist band 57 to thereby control the cock 56 occasionally.

The operational sequence in feeding the liquid medicine into the rubber tunica elastica 11 in the second embodiment is the same as that has been mentioned in the first embodiment and the normal injection to a patient is carried after opening the cock 29 as in the first embodiment.

If desired to increase the flow amount of the liquid medicine, it can be obtained by opening the cock 56 of the flow amount change device 51 to make the supplemental flow through the tube 48 flow into the extended tube 49.

This second embodiment renders the liquid medicine injection effective as in the first embodiment and can increase the flow amount if desired by smoothly controlling the flow amount change device 51 attached to the wrist by the wrist band 57.

The liquid medicine feed pipe 41 is designed to fit the deflated rubber tunica elastica 11 so that in a deflated state a remaining air and liquid medicine in the rubber tunic elastica 11 can be minimized.

Figure 5:
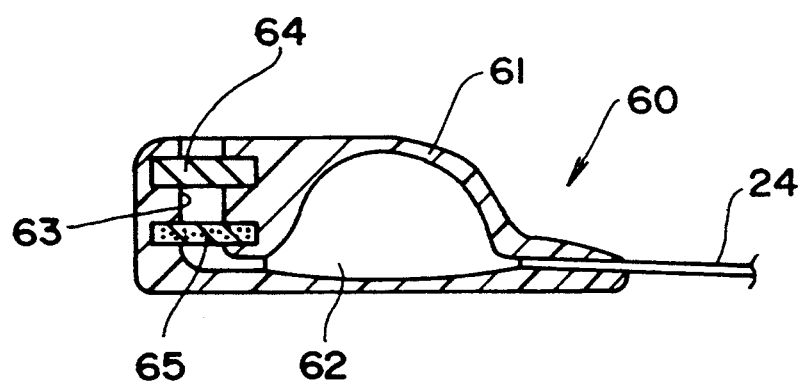
FIG. 5 is a sectional view depicting the third embodiment according to the present invention.
Figure 6:
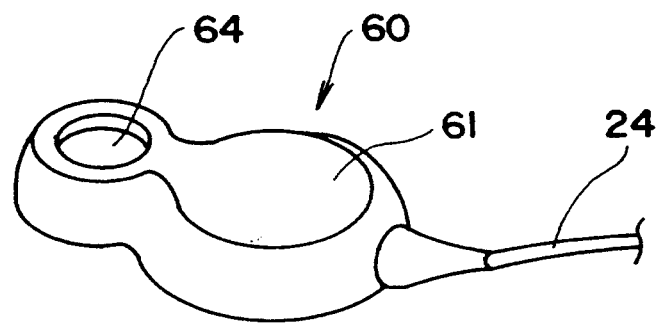
FIG. 6 is a perspective view depicting the third embodiment.

The third embodiment according to the present invention will be described with reference to FIGS. 5 and 6. A liquid medicine injecting device 60 as the third embodiment according to the present invention is a modified form of the device 10 as is applied to the device taught in Japanese Patent Laid-open No. 2-19172 retained in human body. It can be seen that the liquid medicine injecting device 60 is defined by a main body 61 formed by an elastic material such as a flexible plastic to contain the liquid medicine in a liquid medicine receiving portion 62 therein. The liquid medicine receiving portion 62 has a liquid medicine inlet port 63 defined by a filter 65 and a septum 64 utilized as a check-valve such that when a needle to feed the liquid medicine into the portion 62 is released the though hole made therein by the needle is completely choked up.

The liquid medicine receiving portion 62 is adapted to receive the thermoplastic resin tube 24 as the low amount control means at an opposite side of the liquid medicine inlet portion 63. Incidentally, the tube 24 also has the same sectional patterns as described in the first and second embodiments. The forward end of the tube 24 is provided to directly connect to a blood vessel of the patient without a needle.

Accordingly, a refilling process of the liquid medicine into the liquid medicine receiving portion 62 can be conducted by using a general injector through the septum 64.

The necessary pressure to feed the stored liquid medicine in the portion 62 into the human body through the tube 24 is assured by an elastic force of the main body 61.

It is believed that the third embodiment can obtain the same effects as by the thermoplastic resin tube 24 used in the first and second embodiments. It will further be understood that the device 60 is more simple in structure than the conventional one whereby the applicability of the device 60 in the human body becomes preferable. Further, the device 60 does not pain the patient when feeding the liquid medicine into the human body since it does not feed it as taught in the reference wherein a large quantity of the liquid medicine is fed at a time to the patient.

The invention may be embodied in other specific forms without departing from the spirit or essential characteristics thereof. The present embodiments are therefore to be considered in all respects as illustrative and no restrictive, the scope of the invention being indicated by the appended claims rather than by the foregoing description, and all changes which come within the meaning and range of equivalency of the claims are therefore intended to be embraced therein.

In the first embodiment, for example, the filling procedure of the liquid medicine can be conducted through the sliding element 12 provided with a similar cock and check-valve as described in Japanese Patent Laid-open No. 56-102252. The filter 22 and the connector 25 can be configured into a one-piece member. The rubber tunica elastica 11 is intended to serve both the pressure means and the liquid medicine receiving portion but an optional spring can be utilized as the pressure means and the liquid medicine receiving portion may employ a structure defined by a piston and a corresponding cylinder.

The invention is applicable to various injectors for vena, urinary organs, obstetrics and gynecology and the like, and further to a catheter.

EXPERIMENTAL EXAMPLES

The some experimental examples are done to confirm the actual effects according to the present invention.

In each experimental example, characteristics in actual flow, assembling and handling are confirmed, respectively.

The sectional configuration of the tested tube 24 is examined by a photomicrograph and a ratio of Long side/Short side and the differentia are determined with reference to the photomicrograph.

Figure 7:
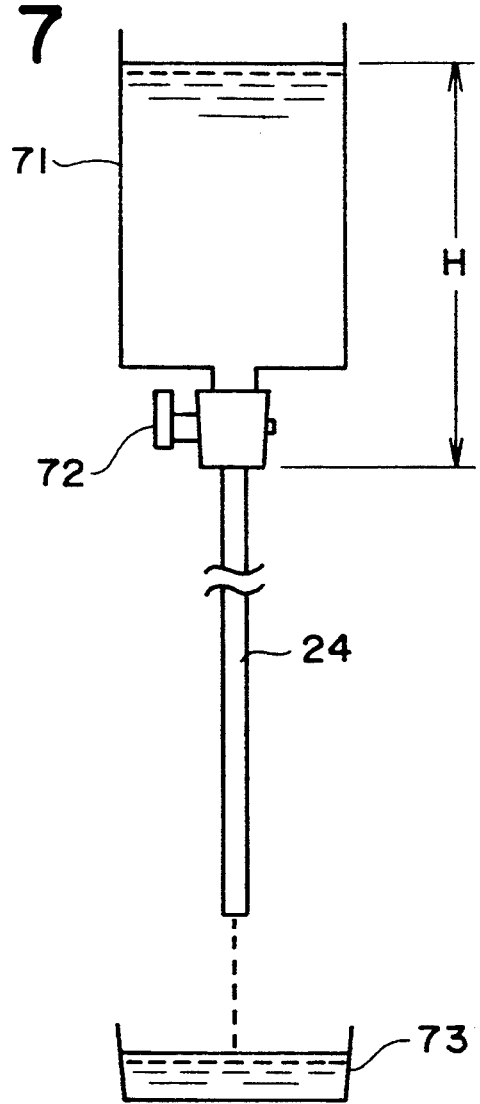
FIG. 7 is a diagrammatic view of an apparatus assembled for conducting several examples.

The flow amount by the tube 24 is measured as shown in FIG. 7 where the tube 24 is connected to a big plastic tank 71 placed over it through a cock 72 provided at a lower end portion of the tank 71. The dropped out purified water in a pan 73 from the distal lower end of the tube 24 is measured by a unit of milliliter/hour or microliter/hour for 24 hours.

The pressure value is obtained by a unit of millimeter water column calculated by a water level in the tank 71 and a distance H from the water level to the upper portion of the tube 24 as shown in FIG. 7.

The characteristic of assembling is evaluated in assembling the complete device as to whether the opening configuration is deformed or whether the tube is folded for use with two legends of "cross" and "circle".

The characteristic of handling is also evaluated with two legends of "cross" and "circle" as to whether the tube is too thin to use or whether the tube is folded for use.

which has a round through hole 91A in its section and is made from the stainless steel or the glass is tested as shown in Table 1.

These tested tubes 91 made from the stainless steel or the glass are not good in assembling and handling.

TABLE 1

| | | TUBE DIFFERENTIA | | | DIFFER- | | | PRESSURE | | |
|---|---|---|---|---|---|---|---|---|---|---|
| | | SHORT SIDE | LONG SIDE | | ENTIA DEGREE | TUBE LENGTH | FLOW AMOUNT | mm WATER | | |
| | SHAPE | a mm | b mm | b/a | $L/\sqrt{S}$ | mm | ml/h | COLUMN | ASSEMBLING | HANDLING |
| EX. EXAM. | FIG. 2 | | | | | | | | | |
| 1 | (A) | 0.03 | 1.7 | 57 | 39 | 1000 | 0.2 | 1400 | ○ | ○ |
| 2 | (B) | 0.02 | 1.7 | 85 | 18 | 1000 | 0.13 | 1400 | ○ | ○ |
| 3 | (C) | 0.01 | 0.14 | 14 | 8 | 40 | 0.2 | 1400 | ○ | ○ |
| 4 | (D) | 0.03 | 0.2 | 7 | 16 | 20 | 0.5 | 1400 | ○ | ○ |
| 5 | (E) | 0.03 | 1.0 | 28 | 54 | 1000 | 0.5 | 1400 | ○ | ○ |
| 6 | (C) | 0.01 | 0.14 | 14 | 8 | 200 | 0.05 | 1400 | ○ | ○ |
| 7 | (A) | 0.03 | 1.7 | 57 | 39 | 40 | 5 | 1400 | ○ | ○ |
| CONT. EXAM. | | | CIRCULAR INNER DIAMETER mm | | | | | | | |
| 1 | FIG. 8 | SUS | 0.1 | 1 | 3.5 | 1000 | 0.3 | 3400 | × | × |
| 2 | FIG. 8 | GLASS | 0.035 | 1 | 3.5 | 19 | 0.5 | 6700 | × | × |
| 3 | FIG. 8 | SUS | 0.15 | 1 | 3.5 | 1000 | 0.5 | 1100 | × | × |

Experimental Examples 1–7

In the 1st experimental example, the tube has the short side of 0.03 mm and the long side of 1.7 mm as its differentia, the tube of which has the outer diameter of 0.5 mm and used as depicted in FIG. 1. Incidentally, the tube 24 is finished with a EVA coating to reach a outer diameter of 3.0 mm by means of an extruder for coating.

The respective tubes 24 in the experimental examples 1–7 have their own differentia which differ from each other and are examined as shown in Table 1 about the ratio of Long side/Short side, length, flow amount, pressure value, sectional configuration and differentia degree given by an expression of $\sqrt{(A/B)}$, wherein the A means an inside measurements of the opening and wherein the B means an area of the opening. Incidentally, the dimensions of the short and long sides shown in FIGS. 2(A), 2(D) and 2(E) are obtained by measuring the width and length of the grooves thereof with a similar way in FIGS. 2(B) and 2(C).

CONTROL EXAMPLES 1–3

Figure 8:
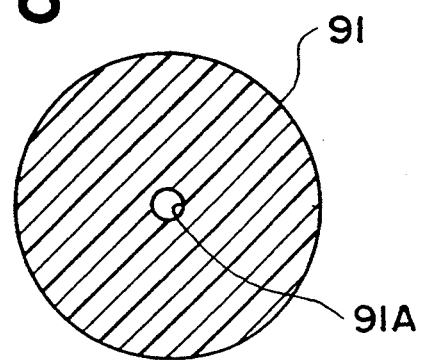
FIG. 8 is a sectional view of a tube used in the control examples.

In order to confirm the effectiveness in using the tube 24, it will be noted from FIG. 8 that another tube 91,

Experimental Examples 8–10

These examples 8–10 are conducted in a state as depicted in FIG. 3 where both the main tube 24 and the supplemental tube 48 optionally opened by the cock 56 are parallely connected to the connector 44 and the needle 31 is applied to the device 40 after the two tubes 24 and 48 flow together, that is, if desired the needle 31 can feed the liquid medicine at two feeding levels, one level of which becomes from the tube 24 only and the other becomes from the both tubes 24 and 48 after opening the cock 56 by the patient.

CONTROL EXAMPLE 4

In this control example 4, the rubber tunica elastica 11 is intentionally pressured to feed the liquid medicine into the human body rapidly, that is 0.5 ml in two seconds. As a result of it, the ratio of the supplemental amount and the constant amount increases rapidly to give an unpleasant feeling to the patient.

The result of measurement is shown in Table 2.

TABLE 2

| | MAIN FLOW | | | SUPPLEMENTAL FLOW | | | RATIO OF SUPPLEMENTAL/ |
|---|---|---|---|---|---|---|---|
| | SHAPE | mm/H | μl/SEC | SHAPE | mm/H | μl/SEC | CONSTANT FLOW |
| EX. EXAM. 8 | FIG. 2 (A) | 0.2 | 0.55 | FIG. 2 (A) | 0.2 | 0.55 | 1 |
| EX. EXAM. 9 | FIG. 2 (A) | 0.2 | 0.55 | FIG. 2 (B) | 0.13 | 0.36 | 0.65 |
| EX. EXAM. 10 | FIG. 2 (A) | 0.2 | 0.55 | FIG. 2 (D) | 0.5 | 1.38 | 2.5 |
| CONT. EXAM. 4 | FIG. 8 | 0.2 | 0.55 | FIG. 8 | 0.5 | 250 | 454.5 |

Experimental Examples 11–15

The tubes used in these experimental examples 11–15 are the same ones as used in the experimental examples 1–5 and are evaluated about blocking states when making one knot or being folded, the results of which are shown in Table 3.

CONTROL EXAMPLES 5-7

The tubes prepared in these control examples 5-7 are made from the stainless steel, the glass, and the vinyl chloride under the same condition as has been mentioned in the experimental examples 11-15.

Accordingly, even if the tube is knotted once or folded, the characteristic opening will not be blocked up to thereby keep the predetermined constant flow amount.

It has been known that the vinyl chloride tube used in the 7th control example for a general blood transfusion tends to be blocked up when being knotted or folded so that it can not maintain a preferable flow.

The stainless tube finished with a resin coating thereon used in the 5th control example is lack of softness to curve without breaking. Even if the same tube without the coating will be used, the same tendency can be confirmed.

The glass tube used in the 6th control example is too hard to be curved so that when being folded it should be broken.

TABLE 3

|  | SHAPE | BLOCK-ING | STATE OF BLOCKING |
|---|---|---|---|
| EX. EXAM. | | | |
| 11 | FIG. 2 (A) | o | NOT PRESENT |
| 12 | FIG. 2 (B) | o | NOT PRESENT |
| 13 | FIG. 2 (C) | o | NOT PRESENT |
| 14 | FIG. 2 (D) | o | NOT PRESENT |
| 15 | FIG. 2 (E) | o | NOT PRESENT |
| CONT. EXAM. | | | |
| 5 STAINLESS | FIG. 8 0.1-0.3 mm* | x | FOLDED AND BROKEN |
| 6 GLASS | FIG. 8 0.035-3 mm* | x | BROKEN |
| 7 VINYL CHLORIDE RESIN | FIG. 8 0.5-2.6 mm* | x | CLOGGED |

In Table 3, the legend "circle" means that the tube does not block up, the "cross" means that the tube blocks up, the configuration marked with "*" means the circle shape and the figures mention the inner-outer diameter.

Accordingly, when the thermoplastic resin tube, having the characteristic sectional configuration as the flow amount control means as has been described above will be used, the flow amount control can be carried out precisely. Further, even if there are contaminant and the like in the liquid medicine or if the tube is folded, twisted, or pressured, the tube is not blocked up to thereby function as a capillary tube and a member for controlling flow amount with a simple structure so that a high productivity and a easy handling can be obtained.

What is claimed is:

1. A liquid medicine injecting device, comprising:
   a liquid medicine receiving portion to store therein a liquid medicine;
   a pressure means for pressurizing the liquid medicine;
   flow amount control means applied to be connected to said liquid medicine receiving portion at one end thereof and made from a thermoplastic resin having a different sectional configuration opening and a predetermined length for conducting two functions as a capillary tube and a member for controlling flow amount all together; and
   a human body fitting tool connecting to the other end of said flow amount control means so that the liquid medicine stored in said liquid medicine receiving portion is fed into a human body through said flow amount control means and said human body fitting tool.

2. The liquid medicine injecting device according to claim 1, wherein a sectional configuration of the tube defining said flow amount control means is arranged by three sets of two different arborescent raised portions each of which is extending from an inner wall surrounding a base round hole.

3. The liquid medicine injecting device according to claim 1, wherein a sectional configuration of the tube defining said flow amount control means is formed into a Y-shape, each stem of the Y being angularly intersecting each other at a same angle of 120 degrees.

4. The liquid medicine injecting device according to claim 3, wherein the Y-shaped opening is formed by uneven surface.

5. The liquid medicine injecting device according to claim 1, wherein a sectional configuration of the tube defining said flow amount control means is arranged by three tapered triangles with one roundly recessed portion at the base each of which extends from an inner wall surrounding a base round hole.

6. The liquid medicine injecting device according to claim 1, wherein a sectional configuration of the tube defining said flow amount control means is arranged by three sets of two different arborescent raised portions each of which is extending from an inner wall with uneven surface surrounding a base round hole.

7. The liquid medicine injecting device according to claim 3, wherein a short side of the each stem shape of the opening is kept within 0.01-0.1 mm and the ratio of the length of the long side of the stem of the short side of the stem is more than 3.

8. The liquid medicine injecting device according to claim 1, wherein the differentia degree of the tube is given by an expression of $\sqrt{(A/B)}$ on or more than 7, the "A" being an inside measurement of the opening and the "B" being an area of the opening.

9. The liquid medicine injecting device according to claim 1, wherein the tube is a single layered tube made from a thermoplastic resin tube selected one from polyethylene (PE), polypropylene (PP), polyacetal (POM), polycarbonate (PC), ABS, polyamide resin or polystyrene (PS) or a coated single layered tube with a thermoplastic polyurethane elastomer.

10. The liquid medicine injecting device according to claim 1, wherein there is provided a supplemental flow control means defined by a thermoplastic resin tube in a parallel state to said flow amount control means between said liquid medicine receiving portion and said human body fitting tool, said supplemental flow control means being provided with a flow on-off means for being manually opened and closed.

11. The liquid medicine injecting device according to claim 10, wherein said supplemental flow control means is a thick tube having little pressure loss.

12. The liquid medicine injecting device according to claim 1, wherein said liquid medicine receiving portion is defined by a tubular rubber tunica elastica, and wherein said pressure means is made by a contractile force of the tubular rubber tunica elastica one end of which directly or indirectly connects to the tube of said flow amount control means.

13. The liquid medicine injecting device according to claim 1, wherein said liquid medicine receiving portion is received and closed up in a protective cover having a water repellent breathing filter.

14. The liquid medicine injecting device according to claim 13, wherein the protective cover is constructed by a cylinder and an associated cap, wherein said liquid medicine receiving portion is a rubber tunica elastica both end of which are opened, and wherein said pressure means is made by a contractile force of the tubular rubber tunica elastica one end of which directly or indirectly connects to the tube of said flow amount control means and the other end of which securely connects to a sliding element reciprocally moving in the protective cover.

15. The liquid medicine injecting device according to claim 14, wherein the rubber tunica elastica has a contractile force of from 1000 to 700 mm water column.

16. The liquid medicine injecting device according to claim 1, wherein said liquid medicine receiving portion is made by a rubber tunica elastica one end of which is opened and the other is closed, wherein said pressure means is made by a contractile force of the tubular rubber tunica elastica, and further comprising a liquid medicine feed pipe in the rubber tunica elastica which is adapted to fit the deflated rubber tunica elastica and connect to the tube of said flow amount control means.

17. The liquid medicine injecting device according to claim 1, wherein said pressure means is a spring.

* * * * *